United States Patent [19]

Ward et al.

[11] Patent Number: 4,655,891
[45] Date of Patent: Apr. 7, 1987

[54] PROCESS FOR THE PHOTOCHEMICAL DEHYDROGENATION OF ALCOHOLS WITH SEMICONDUCTOR POWDER SUSPENSIONS

[75] Inventors: Michael D. Ward, South Euclid; James F. Brazdil, Jr., Mayfield Village; Robert K. Grasselli, Aurora, all of Ohio

[73] Assignee: The Standard Oil Company, Cleveland, Ohio

[21] Appl. No.: 643,151

[22] Filed: Aug. 22, 1984

[51] Int. Cl.$^4$ .............................................. B01J 19/12
[52] U.S. Cl. .................................. 204/157.93; 204/903
[58] Field of Search ................... 204/157.93, 903, 904, 204/905, 157.52

[56] References Cited

U.S. PATENT DOCUMENTS 3,591,476  7/1971  Battaerd ............................. 204/158
4,264,421  4/1981  Bard et al. .................... 204/157.1 R
4,303,486  12/1981 Bard et al. ....................... 204/162 R

FOREIGN PATENT DOCUMENTS 7013639  3/1970  Netherlands .

OTHER PUBLICATIONS

M. A. Malati and N. J. Seager "Further Investigation of the Photo-Induced Oxidation of Normal Primary Alcohols by Anatase Titanium Dioxide", J. Oil Col. Chem. Assoc. 64, pp. 231–233 (1981).

S. Teratani, J. Nakamichi, K. Taya and K. Tanaka "Photocatalytic Dehydrogenation of 2-Propanol over $TiO_2$ and Metal/$TiO_2$ Powders" Bull. Chem. Soc. Japan 55, pp. 1689–1690 (1982).

P. Pichat, J. Herrmann, J. Disdier, H. Courbon and M. Mozzanega "Photocatalytic Hydrogen Production from Aliphatic Alcohols over a Bifunctional Platinum on Titanium Dioxide Catalyst" Nouveau Journal de Chimie, vol. 5, p. 627 (1981).

*Primary Examiner*—Howard S. Williams
*Attorney, Agent, or Firm*—Joseph G. Curatolo; Larry W. Evans

[57] ABSTRACT

A process for the photochemical dehydrogenation of alcohols comprises the steps of forming a suspension of semiconductor powder in the alcohol and photochemically activating the suspension in the presence of an oxidant with illumination having an energy at least equal to the band gap of the semiconductor powder. The process is one carried out at about ambient temperature and with gentle agitation. The semiconductor powder has the general formula $A_xB_yC_z$ where A is selected from Bi, Sn, Pt, Pd, Cu, Fe, W, V, Sb, Mo, Ru or Ag and mixtures thereof; B is Te, Sb, Ti, Cd, Mo, W or V and mixtures thereof; C is O or S; x equals 0.1 to 5; y equals 1 to 3; and z is a number necessary to satisfy the other elements, and is optionally metallized by an element selected from Pt, Pd, Cu or Ag.

24 Claims, No Drawings

PROCESS FOR THE PHOTOCHEMICAL DEHYDROGENATION OF ALCOHOLS WITH SEMICONDUCTOR POWDER SUSPENSIONS

TECHNICAL FIELD

The subject invention relates to a new and useful process for the conversion of alcohols to aldehydes and ketones with a photocatalytically activated semiconductor powder suspension at about ambient temperature and in the presence of an oxidant. This photoactivation is achieved with illumination having an energy at least equal to the band gap of the selected semiconductor powder.

BACKGROUND ART

The conversion of alcohols to aldehydes and diols has been conducted heretofore with high energy radiation in the presence of catalysts. U.S. Pat. No. 3,591,476 discloses the use of a solid catalyst such as CdO, ZnO, alpha alumina, $Al_2O_3$, PbO, $Pb_3O_4$, $Sb_2O_3$, $Bi_2O_3$, $V_2O_5$, $MoO_3$, CoO, CuO and CuO on copper. Suitable high energy radiation sources include accelerated electrons, gamma ray, X-rays and the like. The patent reports a significant increase in product yield when the solid catalyst is employed.

The use of photocatalysis to prepare metallized semiconductor powders, such as $TiO_2$ powder metallized with copper, is described in U.S. Pat. No. 4,264,421. These catalysts have utility, for example, in the photocatlytic decarboxylation of saturated carboxylic acid. Metallizing of the semiconductor powder is disclosed as being achieved with illumination from a 2500 watt Hg-Xe lamp operated at 1600 watts for less than about four hours.

Such a method for the decarboxylation of saturated carboxylic acids on n-type semiconductor powders (e.g., $TiO_2$) is described in a companion patent, U.S. Pat. No. 4,303,486. The major reaction products are the corresponding alkanes and $CO_2$. A suspension of the catalyst in a solution containing the acid is irradiated at ambient temperature. The reaction mixture can be subjected to irradiation in the presence or absence of oxygen and the semiconductor powder, such as $TiO_2$, can be platinized.

The photocatalytic dehydrogenation of alcohols over titanium dioxide catalysts has also been reported by independent investigators. The dehydrogenation of 2-propanol over $TiO_2$ and metal $TiO_2$ powders, where the metal is Ru, Rh, Pd, Ir, Pt, was reported by S. Teritani, J. Nakamishi, K. Taya and K. Tanaka, *Bull. Chem. Soc. Jpn.*, 55, 1688 (1982). The authors found the following reactivity order: $Pt/TiO_2 > Rh/TiO_2 > Pd/TiO_2/Ru/TiO_2 > Ir/TiO_2 > TiO_2$. The irradiation of a suspension of anatase titanium dioxide in normal primary aliphatic alcohols with ultraviolet light to produce aldehydes was reported by M. A. Malati and N. J. Seager, *J. Oil Col. Chem. Assoc.*, 64, 231 (1981). Finally, the dehydrogenation of primary and secondary alcohols at room temperature in gaseous, liquid or aqueous phases over a catalyst comprising a dehydrogenating metal such as Pt over a photosensitive semiconductor such as $TiO_2$ was reported by P. Pichat, J. M. Herrmann, J. Disdier, H. Courbon and M. N. Mozzenega, *Nouv. J. Chim.*, 5, 627 (1981).

Lastly, in Netherlands Pat. No. 7,013,639 there is disclosed the oxidation of hydrocarbons, such as isobutane, in gaseous or vapor phase, said hydrocarbon being passed, admixed with oxygen and at a temperature of not more than 100° C., over a metal oxide catalyst such as $TiO_2$ irradiated with UV light, to produce acetone Despite the teachings of the art, there has not been a recognition of the use of specific semiconductor powders for the photochemical dehydrogenation of primary and secondary alcohols in the presence of a promoter redox couple.

SUMMARY OF THE INVENTION

The process for the photochemical dehydrogenation of alcohols comprises the steps of first forming a suspension of a semiconductor powder in the alcohol. The semiconductor powder has the general formula $A_xB_yC_z$ where A is selected from Bi, Sn, Pt, Pd, Cu, Fe, W, V, Sb, Mo, Ru or Ag and mixtures thereof; B is Te, Sb, Ti, Cd, Mo, W or V and mixtures thereof; C is 0 or S; x equals 0.1 to 5; y equals 1 to 3; and z is a number necessary to satisfy the other elements, and is optionally metallized by an element selected from Pt, Pd, Cu or Ag. The process includes the step of photochemically activating the suspension with illumination having an energy at least equal to the band gap of the semiconductor powder.

PREFERRED EMBODIMENT FOR CARRYING OUT THE INVENTION

The process for the present invention is useful for the dehydrogenation of primary and secondary alcohols, to aldehydes and ketones, respectively. Suitable alcohols are those having from one to about 20 carbon atoms including both saturated and unsaturated species as well as substituted species and cyclic compounds. Typical alcohols include methanol, ethanol, propanol, butanol, hexanol, heptanol, octanol, decanol, dodecanol, isopropanol, isobutanol, sec-butanol, isopentanol, cyclopentanol, cyclohexanol, 3-buten-2-ol and the like. The foregoing description and disclosure of suitable alcohols are meant to be illustrative only of the many examples of alcohols which can be dehydrogenated by the subject process but should not be construed as exhaustive or limiting.

As a practical matter, saturated alcohols having from one to about 10 carbons are preferred while for unsaturated alcohols, a range of from three to about 10 carbons is preferred. Preference is not based upon operability, however, and therefore other alcohols may be treated by this process so long as they are not tertiary. As will be noted hereinbelow, the selectivity for a given product can be controlled by the composition of a particular catalyst, as well as the oxidant and promoter redox couple.

In general, the process of this invention can be conducted at ambient temperatures and is carried out in a slurry reactor using an illuminated suspension of a semiconductor powder as the photocatalyst in a solvent media such as the alcohol or an aqueous solution of the alcohol. The light energy utilized to illuminate the semiconductor photocatalyst should have an energy greater than or equal to the band gap of the semiconductor photocatalyst. A typical light source that can be utilized is a 500 watt mercury lamp. The selected illuminating source and application thereof is not critical, it can vary as to type, intensity, positioning and time of application. Depending on how it is applied to a selected system, the illuminating source may contribute some acceptable amount of heat to the heat of reaction which is normally low.

The general formula of semiconductor materials which can be utilized in the practice of this invention is $$A_xB_yC_z$$

where

A is Bi, Sn, Pt, Pd, Cu, Fe, W, V, Sb, Mo, Ru or Ag and mixtures thereof;
B is Te, Sb, Ti, Cd, Mo, W or V and mixtures thereof;
C is O or S;
x is 0.1 to 5;
y is 1 to 3 and,
z is a number necessary to satisfy the other elements.

The A component can be provided in one of two manners. First, it can be in the catalyst wherein the material comprises elements A and B as mixed oxides or sulfides, depending on what C is, and where it may behave as a redox couple. Second, it can be in the reaction suspension as a redox couple wherein it is available to oxidize reduced species as they arise. At least some of the A elements namely, Pt, Pd, Cu and Ag, can also be employed as a metallized coating on the surface of the semiconductor powder. Metallized e.g., platinized, semiconductor powder can be obtained by methods known in the art such as set forth in U.S. Pat. No. 4,264,421, the subject matter of which is incorporated herein by reference.

As will be demonstrated in the Examples hereinbelow, the presence of the A component as a promoter redox couple is highly favored. Thus, while oxidative dehydrogenation of primary and secondary alcohols can be conducted in the presence of a semiconductor powder, in suspension, and an oxidant with illumination, when the redox couple is employed in the process of the present invention, a dramatic and unexpected increase in the yield of respective aldehyde or ketone results.

The A component is generally present as a soluble species in the solvent media but may also be incorporated into the solid matrix of the photocatalyst. The only requirement is that efficient contact between the surface of the photocatalyst and the component be maintained. Incorporation into the solid matrix of the semiconductor powder can be achieved by combining solutions of the two and allowing the solvent to evaporate. When employed as a soluble species, the desired A component can be added as a salt e.g., cupric nitrate hydrate to the semiconductor/oxidant/alcohol suspension.

Generally, preparation of the semiconductor material is not a feature of the present invention inasmuch as those skilled in the art can readily select the disclosed semiconductor powders and utilize the redox couple in one of the foregoing manners by following known techniques. Thus, the particular steps of incorporating into the solid matrix or forming a suspension are not to be construed as limitations of the present invention.

Although the subject invention has been exemplified with $TiO_2$ as the semiconductor powder, other semiconductors formed by combinations of the A, B and C components can be employed. Several of these, for instance, include $MoO_3$, $WO_3$, $CdS$ and $CuMoO_4$. The semiconductor powder can also be modified, as for instance, by metallizing with platinum or by mixing with another powder such as $TiO_2$ with $MoO_3$.

The reaction requires the presence of an oxidant such as $O_2$, $H^+$ and/or reducible metal ions e.g., $Cu^{2+}$, $Fe^{3+}$, $V^{5+}$, $Sn^{4+}$ and mixtures thereof provided by the A component. When $O_2$ is employed, it may be present in a sealed reaction vessel. The choice of oxidant can also influence the product distribution. The presence of more than one oxidant in the reaction mixture can also affect the product distribution. Where oxygen is not present, A component metals such as copper, present as a soluble species, will provide the oxidant.

A preferred example of the invention is directed toward the oxidative dehydrogenation of n-propanol. The exemplary semiconductor powder was titanium oxide, $TiO_2$ (surface area $\leq 50$ m$^2$/g). When an aqueous suspension of $TiO_2$ containing n-propanol was illuminated in the presence of $Cu^{2+}$ ion under $N_2$, a 13-fold increase in propionaldehyde was observed over the same reaction without the $Cu^{2+}$ ion. When $O_2$ replaced $Cu^{2+}$ as the oxidant, yields of propionaldehyde were greater, however, addition of $Cu^{2+}$ to this mixture resulted in a further 4-fold increase.

Exemplification of this invention includes the dehydrogenation of n-propanol to produce propionaldehyde and of allyl alcohol to produce acrolein. Aqueous suspensions of the semiconductor powder were prepared by combining 50 mg of $TiO_2$ with 8 ml of deionized water and 2 ml of the respective alcohol in a 100 ml water cooled reaction flask. In order to demonstrate the effect of oxidants, various reactions were conducted in a sealed oxygen or nitrogen atmosphere with and without an A redox couple $Cu^{2+}$ which was employed by the addition of 0.23 g of $Cu(N_3)_2.2\frac{1}{2} H_2O$ to the reaction mixture. Several examples were also conducted utilizing a metallized photocatalyst, $Pt-TiO_2$. Each mixture was irradiated with a 500 W mercury lamp for three hours with stirring at ambient temperatures. Gas chromatographic analyses of the mixtures after filtration, revealed the presence of aldehydes as the major product. These have been reported in Tables I and II which follow, along with specific reaction mixtures.

TABLE I

Dehydrogenation of n-Propanol on Illuminated $TiO_2$ and $Pt-TiO_2$ Photocatalysts

| Ex. No. | Catalyst | Oxidant(s) | Propionaldehyde Yield ($\mu$mol) |
|---|---|---|---|
| 1 | $TiO_2$ | $O_2$ | 91.5 |
| 2 | $TiO_2$ | $O_2/Cu^{2+}$ | 360 |
| 3 | $TiO_2$ | $N_2$ | 5.2 |
| 4 | $TiO_2$ | $N_2/Cu^{2+}$ | 69.2 |
| 5 | $Pt-TiO_2$ | $O_2$ | 203 |
| 6 | $Pt-TiO_2$ | $O_2/Cu^{2+}$ | 250 |
| 7 | $Pt-TiO_2$ | $N_2$ | 73.5 |
| 8 | $Pt-TiO_2$ | $N_2/Cu^{2+}$ | 130 |

TABLE II

Dehydrogenation of Allyl Alcohol on Illuminated $TiO_2$ and $Pt-TiO_2$ Photocatalysts

| Ex. No. | Catalyst | Oxidant(s) | Acrolein Yield ($\mu$mol) |
|---|---|---|---|
| 9 | $TiO_2$ | $O_2$ | 103 |
| 10 | $TiO_2$ | $O_2/Cu^{2+}$ | 163 |
| 11 | $TiO_2$ | $N_2$ | 17.6 |
| 12 | $TiO_2$ | $N_2/Cu^{2+}$ | 134 |
| 13 | $Pt-TiO_2$ | $O_2$ | 126 |
| 14 | $Pt-TiO_2$ | $O_2/Cu^{2+}$ | 124 |
| 15 | $Pt-TiO_2$ | $N_2$ | 20.1 |
| 16 | $Pt-TiO_2$ | $N_2/Cu^{2+}$ | 80.7 |

By comparing Examples No. 1 and 2, the promoting effect of the $Cu^{2+}$ ion is readily apparent. Similarly, Examples No. 3 and 4, also show the promoting effect of the $Cu^{2+}$ ion where $N_2$ is present rather than $O_2$. Examples No. 5-8 can be compared in the same manner as Examples No. 1-4, the chief difference being that a platinized semiconductor photocatalyst was substituted for $TiO_2$. Also significant is the fact that Example No. 2 outperformed any of the platinized photocatalysts, establishing that although operative, metallization of the semiconductor photocatalyst is not essential to one mode of the invention. Examples No. 1 and 5 are controls, not part of the present invention, to establish the effect of $TiO_2$ and $Pt$-$TiO_2$ as photocatalysts without a promoter. Similarly, Examples No. 3, 7 and 9 are not part of the present invention where unpromoted photocatalysts were also employed.

With respect to Table II, again the promoting effect of the $Cu^{2+}$ ion is readily apparent by comparing Examples No. 10 and 12 with Examples No. 9 and 11. Four platinized examples are also provided, as in Table I, where essentially Examples No. 9-12 were repeated with $Pt$-$TiO_2$ in lieu of $TiO_2$. The use of two oxidants in Example No. 10 increased the yield of acrolein over any of the metallized catalysts. Examples No. 9, 11, 13 and 15 are not part of the present invention, as unpromoted photocatalysts were employed for comparative purposes.

Based upon the foregoing results, it can be seen that the process of the present invention is able to effect dehydrogenation of alcohols at ambient temperatures i.e., about 25° C.; that it is highly selective to desirable products; and that metallized, e.g., platinized, semiconductors are not necessary. Variables, in addition to the basic semiconductor photocatalyst $B_yC_z$ selected, include the use of the promoter redox couple supplied by the A component and the oxidants selected.

Thus, it is to be understood that all of the variables, those disclosed as well as those that are within the existing skill in the art, fall within the scope of the claimed invention and that the subject invention is in no way limited by the examples and respective tables set forth herein. These have been provided merely to provide a demonstration of operability and, therefore, the selection of alcohols, redox couple promoters, oxidants, solvents, processing steps and parameters and the like can readily be determined without departing from the spirit of the invention herein disclosed and described. Moreover, the scope of the invention shall include all modifications and variations that fall within the scope of the attached claims.

We claim:

1. A process for the photochemical dehydrogenation of primary and secondary alchols comprising the steps of:
    forming a suspension of a semiconductor powder and a redox couple in the alcohol, said semiconductor powder having the general formula $A_xB_yC_z$ where A is selected from Bi, Sn, Pt, Pd, Cu, Fe, W, V, Sb, Mo, Ru or Ag and mixtures thereof; B is Te, Sb, Ti, Cd, Mo, W or V and mixtures thereof; C is O or S; x equals 0.1 to 5; y equals 1 to 3; and z is a number necessary to satisfy the other elements,
    wherein said semiconductor powder is optionally metallized by an element selected from Pt, Pd, Cu or Ag and
    said redox couple contains an A element as a separate component of said suspension which is introduced by addition of a salt thereof to said suspension; and
    photochemically activating said suspension in the presence of an oxidant with illumination having an energy at least equal to the band gap of said semiconductor powder.

2. A process for the photochemical dehydrogenation of alcohols, as set forth in claim 1, said process being carried out at about ambient temperature and with gentle agitation of said mixture.

3. A process for the photochemical dehydrogenation of alcohols, as set forth in claim 1 wherein said suspension additionally contains water and said oxidant is $O_2$.

4. A process for the photochemical dehydrogenation of alcohols, as set forth in claim 3, wherein said alcohol is n-propanol.

5. A process for the photochemical dehydrogenation of alcohols, as set forth in claim 3, wherein said alcohol is allyl alcohol.

6. A process for the photochemical dehydrogenation of alcohols, as set forth in claim 1, where said A component forms a solid matrix with said semiconductor powder.

7. A process for the photochemical dehydrogenation of alcohols, as set forth in claim 1, wherein said A component is Cu and said semiconductor powder is formed by combining $TiO_2$ and $Cu(NO_3)_2.2\frac{1}{2}$ $H_2O$.

8. A process for the photochemical dehydrogenation of alcohols, as set forth in claim 7, wherein said suspension additionally contains water and said oxidant is $Cu^{2+}$.

9. A process for the photochemical dehydrogenation of alcohols, as set forth in claim 8, wherein said alcohol is n-propanol.

10. A process for the photochemical dehydrogenation of alcohols, as set forth in claim 8, wherein said alcohol is allyl alcohol.

11. A process for the photochemical dehydrogenation of alcohols, as set forth in claim 8, wherein said oxidant additionally comprises oxygen.

12. A process for the photochemical dehydrogenation of alcohols as set forth in claim 11, wherein said alcohol is n-propanol.

13. A process for the photochemical dehydrogenation of alcohols, as set forth in claim 11, wherein said alcohol is allyl alcohol.

14. A process for the photochemical dehydrogenation of alcohols, as set forth in claim 1, wherein said A component is Cu and said semiconductor powder is metallized.

15. A process for the photochemical dehydrogenation of alcohols, as set forth in claim 14, wherein said metallizing element is Pt and said semiconductor powder is formed by combining platinized $TiO_2$ and $Cu(NO_3)_2.2\frac{1}{2}$ $H_2O$.

16. A process for the photochemical, dehydrogenation of alcohols, as set forth in claim 15, wherein said suspension additionally contains water and said oxidant is $Cu^{2+}$.

17. A process for the photochemical dehydrogenation of alcohols, as set forth in claim 16, wherein said alcohol is n-propanol.

18. A process for the photochemical dehydrogenation of alcohols, as set forth in claim 16, wherein said alcohol is allyl alcohol.

19. A process for the photochemical dehydrogenation of alcohols, as set forth in claim 16, wherein said oxidant additionally comprises oxygen.

20. A process for the photochemical dehydrogenation of alcohols, as set forth in claim 19, wherein said alcohol is n-propanol.

21. A process for the photochemical dehydrogenation of alcohols, as set forth in claim 19, wherein said alcohol is allyl alcohol.

22. A process for the photochemical dehydrogenation of alcohols, as set forth in claim 1, wherein said alcohols are selected from the group consisting of saturated and unsaturated alcohols having from one to about 20 carbon atoms.

23. A process for the photochemical dehydrogenation of alcohols, as set forth in claim 1, said illumination being derived from a 500 watt mercury lamp.

24. A process for the photochemical dehydrogenation of alcohols, as set forth in claim 1, wherein said oxidant is selected from the group consisting of $O_2$, $H^+$, $Cu^{2+}$, $Fe^{3+}$, $V^{5+}$, $Sn^{4+}$ and mixtures thereof.

* * * * *